United States Patent
Bewsher et al.

(10) Patent No.: US 10,383,547 B2
(45) Date of Patent: Aug. 20, 2019

(54) ANTIOXIDANT STABILISER FOR POLYMERS

(71) Applicant: Aquaspersions Ltd., Halifax, West Yorkshire (GB)

(72) Inventors: Alan Bewsher, Ripponden (GB); Paul Smith, Halifax (GB); Michael Richardson, Elland (GB)

(73) Assignee: AQUASPERSIONS LTD., Halifax, West Yorkshire (GB)

( * ) Notice: Subject to any disclaimer, the term of this patent is extended or adjusted under 35 U.S.C. 154(b) by 96 days.

(21) Appl. No.: 15/116,128

(22) PCT Filed: Feb. 2, 2015

(86) PCT No.: PCT/EP2015/052047
§ 371 (c)(1),
(2) Date: Aug. 2, 2016

(87) PCT Pub. No.: WO2015/114131
PCT Pub. Date: Aug. 6, 2015

(65) Prior Publication Data
US 2018/0110443 A1   Apr. 26, 2018

(30) Foreign Application Priority Data

Feb. 3, 2014  (EP) .................................... 14153646

(51) Int. Cl.
| A61K 9/00 | (2006.01) |
| A61B 5/087 | (2006.01) |
| A61B 5/00 | (2006.01) |
| A61B 5/097 | (2006.01) |
| C08K 5/00 | (2006.01) |
| C08K 5/13 | (2006.01) |
| C08K 5/134 | (2006.01) |
| C08K 5/375 | (2006.01) |

(52) U.S. Cl.
CPC .......... *A61B 5/0878* (2013.01); *A61B 5/0004* (2013.01); *A61B 5/0082* (2013.01); *A61B 5/097* (2013.01); *A61B 5/725* (2013.01); *A61B 5/7225* (2013.01); *A61B 5/742* (2013.01); *A61B 5/7405* (2013.01); *A61B 5/746* (2013.01); *C08K 5/005* (2013.01); *C08K 5/13* (2013.01); *C08K 5/1345* (2013.01); *C08K 5/375* (2013.01); *A61B 2503/06* (2013.01); *A61B 2503/40* (2013.01); *A61B 2560/0214* (2013.01); *A61B 2560/0443* (2013.01)

(58) Field of Classification Search
CPC .................................................... A61B 5/0878
See application file for complete search history.

(56) References Cited

U.S. PATENT DOCUMENTS

| 2001/0044518 A1 | 11/2001 | Hoffmann et al. |
| 2003/0144395 A1 | 7/2003 | Broussard et al. |
| 2008/0249214 A1 | 10/2008 | Wegmann et al. |

OTHER PUBLICATIONS

WO patent application No. PCT/EP2015/052047, International Search Report and Written Opinion dated Apr. 17, 2015.

*Primary Examiner* — Paul W Dickinson
(74) *Attorney, Agent, or Firm* — Weaver Austin Villeneuve & Sampson LLP

(57) ABSTRACT

A stabilizer for an organic polymer comprising
  a) poly (dicyclopentadiene-co-p-cresol) (Formula 1);
  b) a sterically hindered phenol of Formula II; and
  c) an alkyl thio methyl phenol of Formula III; and
  d) and optionally a phosphate antioxidant.

20 Claims, No Drawings

ANTIOXIDANT STABILISER FOR POLYMERS

This invention relates to compositions useful for stabilising organic polymers especially natural or synthetic rubbers and other elastomers against oxidative degradation and spoilage. This invention also relates to methods of preparing aqueous dispersions of these compositions and their use in stabilisation of polymers.

Synthetic rubbers are elastomers which can be made using a water-based process in which monomers are polymerised via free-radical emulsion polymerisation in the presence of surfactants. The resulting emulsions comprise an aqueous dispersion of polymer particles. These particles may be coagulated, separated from the water and then dried to form solid rubber or maintained for use in its emulsion form. Natural and synthetic elastomers based on monomers containing unsaturation are inherently susceptible to oxidative degradation and it is standard practice to add one or more antioxidants to them.

The ageing of organic polymers or vulcanizates thereof can lead to a change in various properties such as increased hardness or brittleness of the polymers. Alternatively, softening, loss of elastomeric properties or of mechanical strength may occur. Cracking, surface changes or other changes, such as the electric properties, may be observed. Undesirable odours and discolouration phenomena also often occur.

In order to prevent or reduce said ageing processes it is known to add antioxidant compounds. These can be grouped into four main categories:
(i) mono- or oligofunctional secondary aromatic amines;
(ii) mono- or oligofunctional substituted phenols;
(iii) heterocyclic mercapto group containing compounds andthioesters; and
(iv) phosphites The effect of anti ageing compounds typically slows down when the polymer or vulcanizate to be protected is exposed to higher temperatures, in particular for longer time periods. It is desirable that the anti ageing compounds do not have a colouring effect, but provide a good colour stability to the rubber or vulcanizate thereof and may be used in combination with peroxide or sulfur based vulcanizing agents. Some of the known anti ageing compounds are toxic. Besides the diphenyl amines this applies to phenolic antioxidants like Vulkanox® BKF which is categorized as H361f, and is suspected of damaging fertility.

As there is an increasing need for high ageing stability of rubbers and vulcanizates thereof with regard to storage and colour stability, in particular on exposure to high temperatures, it is a continuing task to provide new and improved concepts for preventing and reducing the ageing processes in rubbers and vulcanizates. This includes reducing the necessary amount of anti-ageing compounds to the minimum without lowering the stabilizing effect.

Examples of rubbers which can be stabilized according to the present invention are:
NBR nitrile rubbers as defined in more detail below,
HNBR partially or fully hydrogenated nitrile rubbers as defined in more detail below,
SBR styrene-butadiene copolymers, including cgboxylated derivatives thereof,
CR polychloroprene,
BR polybutuiliene,
IIR isobutylene-isoprene copolymers, preferably with isoprene contents of 0.5 to 10% by weight,
BIIR brominated isobutylene-isoprene copolymers, preferably with bromine contents of 0.1 to 10% by weight,
CIIR chlorinated isobutylene-isoprene copolymers, preferably with chlorine contents of 0.1 to 10% by weight,
ABR butadiene-$C_{14}$-alkyl acrylate copolymers,
NIR acrylonitrile isoprene rubber
SIR styrene isoprene rubber
IR polyisoprene,
NR natural rubber
ENR epoxidized natural rubber, or mixtures thereof.

The storage and colour stability of rubbers such as nitrile rubbers, styrene butadiene rubbers ("SBR") or other types are frequently problematic. For the present purposes, storage-stable means that the Mooney viscosity changes as little as possible during prolonged storage times, in particular at high temperatures; and, colour stable means that the rubber shows values $\Delta E$ as small as possible as determined according to CIEDE 2000 after storage at high temperatures.

For elastomers which are manufactured using a water-based process, it is highly desirable to add an aqueous dispersion of the antioxidant to the rubber emulsion. This is to ensure the most effective and efficient incorporation of antioxidant into the final polymer. Currently used antioxidant systems comprise single phenolic antioxidants or a combination of a phenolic antioxidant with a thioester antioxidant. A commonly used phenolic antioxidant is a butylated reaction product of p-cresols and dicyclopentadiene (CAS 68610-51-5) commonly known as Antioxidant L (available commercially under the trade names Wingstay L, Lowinox CPL and lonol LC) which has been used as a dispersion either alone or in combination with a thioester such as dilaurylthiodipropionate (CAS 123-28-4). Alternatively 4,6-bis(octylthiomethyl)-o-cresol (CAS 110553-27-0) commonly known as Antioxidant 1520 has been used in combination with a phosphite antioxidant, such as trisnonylphenylphosphite (CAS 26523-78-4), commonly known as TNPP. Another commonly used antioxidant is 2,2'-methylenebis(6-tert-butyl-4-methyl-phenol) (CAS 119-47-1); commonly known as Antioxidant 2246, which has health and safety concerns relating to health of the unborn child (Risk phrase R61).

There is an ongoing need to improve the protection of such polymers against oxidative degradation because this has a deleterious effect on aesthetic and mechanical properties. There is also a need to respond to health and safety concerns relating to some of the currently available antioxidant technologies.

WO-A-2001/081458 discloses a stabilising mixture of two sterically hindered phenolic esters which remain liquid after having been heated together in order to be of use for stabilisation of solid rubbers. The use of such a preparation is inherently inefficient in the stabilisation of aqueous polymer dispersions as the antioxidant mixture is not fully compatible with an aqueous polymer.

EP-A-0 488 550 describes stabilizer compositions comprising 1) sulfide having one or more sulfide groups —$CH_2$—S—$CH_2$—R wherein R is $C_1$-$C_{20}$ alkyl or alkyl alkanoate or 2,4-bis(n-octylthiol)-6-4-hydroxy-3',5'-di-tert-.butylanilino)1,3,5-triazin and at least two hindered phenols (2) and (3) one of which (3) is less sterically hindered than the other (2). Such compositions can be incorporated into polymers to make polymer additives. These polymer additives can provide polymeric products having improved physical and mechanical properties. They are used in high concentrations of 1 to 4% by weight of the polymer and the focus lies on stabilizing acrylate-based rubbers. The use thereof shows some synergistic effect, however, there is neither any showing of an improved stability of the rubber's molecular weight nor any disclosure or teaching of how to reduce the amount of the stabilizing system.

U.S. Pat. No. 5,116,534 discloses a combination of (i) a phenolic antioxidant, (ii) a thiodipropionic acid ester and (iii) a phosphite. Alkyl substituted phenyl phosphites such as TNPP (tri-nonylphenylphosphite) are emphasized. Nowadays these phosphites, are considered harmful in view of their toxic by-products, in particular nonylphenol. U.S. Pat. No. 5,116,534 does not disclose whether the stabilizers are suited to increase the colour stability of the polymers.

WO-A-2009/138342 discloses the use of a combination of
a) a sterically hindered phenol bearing at least one sulfide group of the following formula

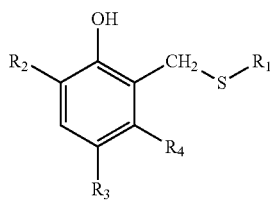

wherein
R$_1$ is C$_8$-C$_{12}$ alkyl
R$_2$ is hydrogen, C$_1$-C$_{12}$alkyl, cyclohexyl, 1-methylcyclohexyl, benzyl, α-methylbenzyl, α,α-dimethylbenzyl or —CH$_2$—S—R$_1$
R$_3$ is C$_1$-C$_{12}$ alkyl, benzyl, α-methylbenzyl, α,α-dimethylbenzyl or —CH$_2$—S—R$_1$, and
R$_4$ is hydrogen or methyl, and
b) a styrenated diphenylamine of the formula

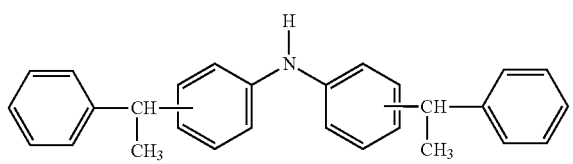

for stabilizing emulsion polymers or rubber latices. However, diphenyl amines are toxic.

EP-A-0 439 427 describes aqueous emulsions which comprise at least (A) one phenolic antioxidant, and/or (B) one thio dipropopionic acid ester and/or (C) an organic phosphite, a surfactant being a salt of an organic acid, and an alcohol.

WO2005/023886 discloses the stabilization of a) methylmethacrylate-butadiene polymers styrene graft polymers using b) a sterically hindered phenolic antioxidant of formula (I), (II) or (III) or a mixture thereof

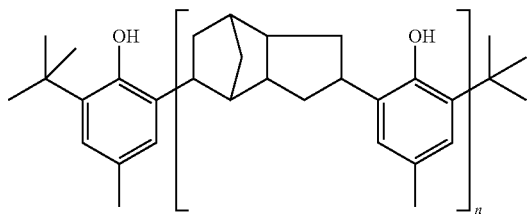

(I)

with n being from 1 to 10

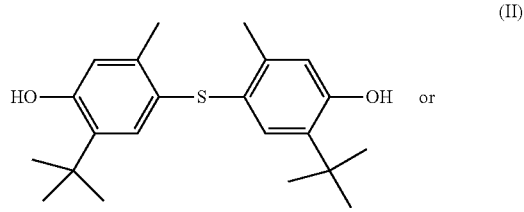

(II)

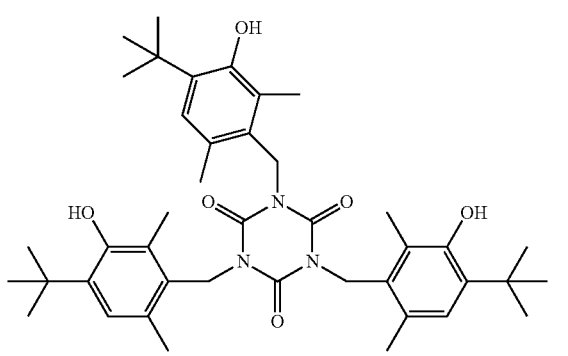

(III)

and c) a thioether differing from that of formula (II).

WO-A-2002/14419 discloses salts of sterically hindered phenols which are used for stabilizing rubbers. These stabilizers are characterized by comprising at least two phenolic hydroxy groups. Preferred sterically hindered phenolic compounds are those of the following formula

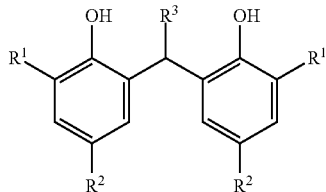

wherein R$^1$, R$^2$, and R$^3$ may identical or different, R$^1$, R$^2$ are C$_1$-C$_{12}$ alkyl or C$_5$-C$_8$ cycloalkyl and R$^3$ is hydrogen, C$_1$-C$_8$ alkyl or C$_5$-C$_6$ cycloalkyl. However, there is no disclosure regarding improvement of the stabilizing efficiency by using specific stabilizers in combination.

WO-A-2001/081458 discloses liquid stabilizing mixtures for organic polymers comprising:
a) a liquid compound belonging to the group of sterically hindered phenols consisting of esters or mixtures of esters having general formula (I)

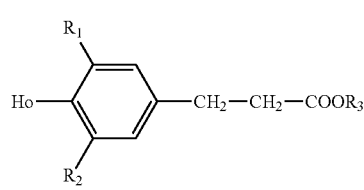

(I)

wherein
R$_1$ and R$_2$ are the same or different, represent a linear or branched C$_1$-C$_{18}$ alkyl group;

$R_3$ represents a linear or branched $C_8$-$C_{18}$ alkyl group, or one of the following groups:

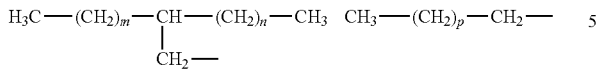

wherein m and n are integers independently from 0 to 11, extremes included, and m+n is 10 or 11, and p is 12 or 13;
b) a solid compound belonging to the group of sterically hindered phenols having the following formula

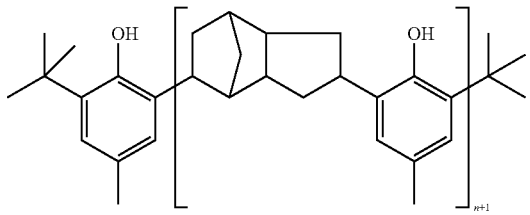

wherein n is an integer ranging from 0 to 10, extremes included.

The stabilising mixture is said to be liquid and is prepared by heating the components together. An inherent problem associated with this mixture is an insufficient compatibility with aqueous polymer dispersions. It is disclosed in WO-A-2001/81458 that such a mixture may be used in combination with further stabilizers, and many classes of compounds are listed. There is no disclosure of any specific combination of stabilizers which might improve the stabilizing effect on rubbers synergistically.

In summary, it can be said that no non-toxic stabilizing system has been described which provides an improved stability for rubbers with regard to Mooney viscosity stability.

It is therefore an object of the present invention to provide a stabiliser which gives unsaturated rubbers good storage stability with regard to Mooney viscosity and colour stability, which does not include toxic or environmentally hazardous compounds and at the same time affords good vulcanization profile and advantageous mechanical properties.

According to a first aspect of the present invention, a stabiliser for an organic polymer mixture comprises one or more compounds from group (a), one or more compounds from group (b) and one or more compounds from group (c) wherein (a), (b), and (c) are as follows:
(a) poly (dicyclopentadiene-co-p-cresol) of Formula I;

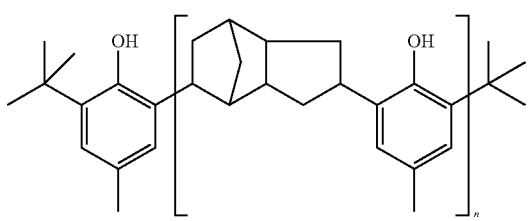

wherein
n is an integer in the range of from 1 to 10,
(b) a sterically hindered phenol of Formula II; and

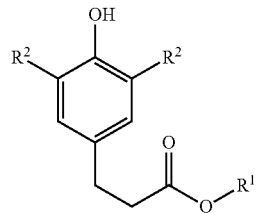

wherein
$R^1$ is hydrogen; straight chain or branched, saturated or one or more times unsaturated, unsubstituted or substituted alkyl; saturated or one or more times unsaturated carbocyclyl or hetercyclyl; aryl; heteroaryl, arylalkyl, heteroarylalkyl, polyoxyalkylene ether, preferably polyoxyethylene ether or polyoxypropylene ether or polyoxyethylene-oxypropylene ether; and
$R^2$ are identical or different and mean straight chain or branched $C_1$-$C_6$ alkyl or $C_5$-$C_6$cycloalkyl;
(c) an alkyl thio methyl phenol antioxidant of Formula III:

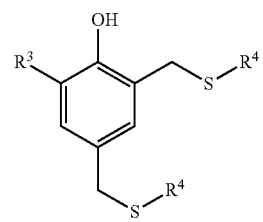

$R^3$ is straight chain or branched $C_1$-$C_{14}$ alkyl; and
$R^4$ is hydrogen, straight chain or branched, saturated or one or more times unsaturated, unsubstituted or substituted alkyl; saturated or one or more times unsaturated carbocyclyl or hetercyclyl; aryl; heteroaryl, arylalkyl, heteroarylalkyl, alkoxy, aryloxy, heteroaryloxy, alkylthio or arylthio.

In preferred formulations the phosphite antioxidant, where present, is selected from the group consisting of:
tris (nonylphenyl) phosphite;
tris (2,4-di-t-butyl phenyl) phosphite;
other alkylaryl phosphites and mixtures thereof.

The present invention provides aqueous dispersions of antioxidants and combinations of antioxidants which may improve aesthetic and mechanical properties of polymers compared to those available using currently available technologies.

The stabiliser may comprise a mixture of one compound selected from each of the groups consisting of (a), (b), and (c) and an optional compound selected from group (d).

Alternatively, two or more compounds may be selected from each of one or more of groups (a), (b), and (c) together with a single compound from the remaining group or groups.

Particularly advantageous stabilisers comprise two or more compounds selected from groups (a), (b) and (c).

In preferred compositions the ratio by weight of (a):(b):(c) is in the ranges of 1 to 100:30:1 to 100.

Preferably the ratio is 5 to 30:5 to 30:5 to 30.
More preferably the ratio is 5 to 30:10:5 to 30.
Most preferably the ratio is 10:10:10.
Another most preferred ratio is 20:10:20.

When compound (d) is present the amount is 1-50% of the total mass of antioxidant, more preferably 5-30% of the total mass of antioxidant.

According to a second aspect of the present invention a stabiliser for an organic polymer mixture comprises a mixture of one or more compounds selected from group (a) as defined above and one or more compounds selected from group (c) as defined above.

In a particularly preferred embodiment the stabiliser comprises a single compound selected from group (a) and a single compound selected from group (c).

Preferably the stabiliser in accordance with the second aspect consists of the compounds selected from groups (a) and (c) in the sense that no further antioxidant may be present.

In a preferred composition the ratio by weight of (a):(c) is in the range of about 4:1 to about 1:1, preferably about 3:1 to about 1:1, more preferably about 2:1 to about 1:1.

Alternative ranges of (a):(c) are 3:2 to 2:4, preferably 3:2 to 2:3. A particularly advantageous composition has the ratio 1:1.

According to a third aspect of the present invention a stabiliser for an organic polymer mixture comprises a mixture of one or more compounds selected from group (b) as defined above and one or more compounds selected from group (c) as defined above.

In a particularly preferred embodiment the stabiliser comprises a single compound selected from group (b) and a single compound selected from group (c).

Preferably the stabiliser in accordance with the second aspect consists of the compounds selected from groups (b) and (c) in the sense that no further antioxidant may be present.

In a preferred composition the ratio by weight of (b):(c) is in the range of about 4:1 to about 1:1, preferably about 3:1 to about 1:1, more preferably about 2:1 to about 1:1, especially about 1:1.

In preferred embodiments a minimum amount of component (c) is employed.

Compositions in accordance with the second and third aspects of this invention have the advantage that stabilised rubbers are whiter in colour and better preserved.

According to a fourth aspect of the present invention a method of preparation of a stabiliser in accordance with a previous aspect of this invention comprises the steps of:
heating a mixture of the compounds selected from groups (a), (b), (c) and
optionally (d), to a temperature above 60° C. to form a molten mixture;
adding a surfactant to the molten mixture;
adding hot water to the molten mixture;
stirring the aqueous mixture; and
optionally adding one or more further ingredients.

A specific example of the component (a) is commonly referred to as Antioxidant L. This compound has CAS 68610-51-5.

A particularly preferred compound from group (b) is octadecyl-3-(3,5-di-tert-butyl-4-hydroxyphenyl) propionate, commonly referred to as Antioxidant 1076. This compound has CAS 2082-79-3.

A particularly preferred compound is 2-methyl-4,6-bis[octylthiomethyl]-phenol, commonly referred to as Antioxidant 1520. This compound has CAS110553-27-0.

In advantageous embodiments of the invention the antioxidants are a mixture of Antioxidants L, 1076 and 1520.

In a further embodiment, the antioxidant mixture can also be composed of any two of these antioxidants and optionally a phosphite of Formula IV.

Where two antioxidants are used a preferred combination is component (a) and component (c).

More preferably one of the antioxidants is Antioxidant L and most preferably Antioxidant L is used in combination with Antioxidant 1520 either with or without the further antioxidants (b) and (d).

The phosphite antioxidant (d) preferably comprises one or more phosphites selected from the group consisting of:
tris (nonylphenyl) phosphite;
(TNPP), tris;
tris (2,4-di-t-butylphenyl) phosphite;
or a phosphite sold under the trade mark Weston 705 (Addivant USA LLC)

The composition may further comprise one or more additional antioxidants or synergists. Preferred additional antioxidants or synergists are selected from the group consisting of: tocopherols, phenolics, thioesters, phosphonates, triazines, amines, benzyl compounds, and ascorbic acid. Other additives, for example light stabilisers, catalysts and optical brighteners, may also be admixed with these antioxidants and synergists.

In normal industrial practice it is desirable to use aqueous dispersions of the above compositions in order to maximise compatibility and efficiency of incorporation. A dispersion may be defined as a heterogeneous mixture of organic material suspended in water. In order to provide these, further ingredients may be required and comprise one or more of: water, surfactants, thickening agents, preservatives and adjuvants such as antifoams.

Surfactants may be anionic, non-ionic or cationic in nature. A preferred surfactant may comprise a mixture of a fatty acid, for example oleic acid and alkali, for example aqueous potassium hydroxide.

A preferred thickening agent may be a hydrocolloid, preferably xanthan gum. This is preferred in order to ensure long term stability during storage and transportation.

Alternatively a solution of such mixtures in water or organic solvent may be employed.

A stabiliser dispersion of the present invention may be manufactured by heating and mixing the melted ingredients. A surfactant may be added. A suitable surfactant may comprise a mixture of long chain aliphatic acid, for example, oleic acid and alkali, for example, aqueous potassium hydroxide. The resultant mixture may be stirred with hot water and a hydrocolloid, for example xanthan gum to form a suspension which may be cooled. Any further ingredients, for example a biocide may be added before packaging and storage or distribution.

The stabiliser of the present invention may be used to stabilise a wide variety of rubbers and other polymeric materials, including: nitrile rubbers; partially or fully hydrogenated nitrile rubbers; styrene-butadiene copolymers, including carboxylated derivatives; polychloroprene; polybutadiene; isobutylene-isoprene copolymers; brominated isobutylene-isoprene copolymers; chlorinated isobutylene-isoprene copolymers; butadiene-$C_{1-4}$-alkyl acrylate copolymers; acrylonitrile isoprene rubbers; styrene isoprene rubbers; styrene isoprene rubbers; polyisoprene; natural rubbers; epoxidized natural rubber; and mixtures thereof.

The preparation of the nitrile rubbers by polymerization of the above mentioned monomers is adequately known to those skilled in the art and is comprehensively described in the literature. Nitrile rubbers which can be used for the purposes of the invention are also commercially available, e.g. as products from the product range of the Perbunan® and Krynac® grades of Lanxess Deutschland GmbH.

Rubbers with the previously disclosed stabilisers and in particular stabilized nitrile rubbers surprisingly show very good storage and colour stability, a positive processing behaviour and unchanged positive mechanical and dynamical properties.

Good storage stability of a rubber is given if the Mooney viscosity is as stable as possible over a prolonged period of time, especially at relatively high temperatures.

The storage stability is usually determined by storing the unvulcanized rubber for a defined period of time at elevated temperature (also referred to as hot air storage) and determining the difference between the Mooney viscosities before and after this storage at elevated temperature. Since the Mooney viscosity of rubber usually increases during hot air storage, the storage stability is characterized by the difference of Mooney viscosity after storage minus Mooney viscosity before storage.

This will be shown on the example of stabilized nitrile rubbers in the following:

The stabilized rubbers may be prepared according to the invention by bringing the stabiliser components into contact with the rubber.

Such incorporation may be achieved in various manners
(1) during the preparation of the rubber, including the polymerisation and the work-up of the rubber, the latter comprising the coagulation and isolation,
(2) in one or more further chemical conversion steps subsequently to the preparation of the rubber such as a metathesis reaction, a hydrogenation reaction or a polymer analogous reaction such as grafting, and/or
(3) during the preparation of vulcanizable mixtures based on the nitrile rubber or the nitrile rubber after being subjected to one or more further chemical conversion before cross-linking.

The addition of the components in any of the aforementioned steps may be realized in different ways:

Each component (a), (b), (c) and (d) can be added separately. Different mixtures of the three components can be combined. Typically the three components, whether added singly or in any type of combination, are used as a dispersion or emulsion.

Percentages and other amounts referred to in this specification are by weight unless indicated otherwise. Percentages are selected from any ranges quoted to total 100%.

The invention is further described by means of example but not in any limitative sense.

EXAMPLE 1

Antioxidant 1520 (16.67% w/w) and Antioxidant 1076 (16.67% w/w) were added to a vessel and heated with high shear stirring. When the mixture was molten poly-dicyclopentadiene-co-p-cresol (16.67% w/w) was added. The mixture was heated to 115° C. for 15 minutes and cooled to 95° C. A mixture of oleic acid (3.34% w/w) and 50% strength aqueous potassium hydroxide (1.31% w/w) was added and the mixture was stirred for 5 minutes. Hot water at 80° C. (45.07%) was added at a rate of 6/minute. When 0.15% of the total water charge remained to be added, xanthan gum (0.08%) was sprinkled onto the solution and the remaining water was added. The mixture was allowed to cool to 40° C., biocide (Acticide (MBL) 0.20%) was added with stirring and the mixture was packaged for use or distribution as required.

The resultant antioxidant was a solid in water suspension having a viscosity of 250-450 cP and pH 9.0-11.5, particle size d95%<3 μm and a total solids content of 53-55%.

EXAMPLE 2

Antioxidant 1520 (25% w/w) was added to a vessel and heated with high shear stirring. At 60° C., poly-dicyclopentadiene-co-p-cresol (25% w/w) was added. The mixture was heated to 115° C. for 30 minutes and cooled to 95° C. A mixture of oleic acid (3.34% w/w) and 50% strength aqueous potassium hydroxide (1.31% w/w) was added and the mixture was stirred for 5 minutes. Hot water at 80° C. (45.07%) was added at a rate of 6/minute. When 0.15% of the total water charge remained to be added, xanthan gum (0.08%) was sprinkled onto the solution and the remaining water was added. The mixture was allowed to cool to 40° C., biocide (Acticide (MBL) 0.20%) was added with stirring and the mixture was packaged for use or distribution as required.

The resultant antioxidant was a solid in water suspension having a viscosity of 400-600 cP and pH 9.0-11.5, particle size d 95%<3 μm and a total solids content of 53-55%.

EXAMPLE 3

Antioxidant 1520 (12.5% w/w) was added to a vessel and heated with high shear stirring. At 60° C. Antioxidant 76 (37.5% w/w) was added. The mixture was heated to 115° C. for 30 minutes and cooled to 95° C. A mixture of oleic acid (3.34% w/w) and 50% strength aqueous potassium hydroxide (1.31% w/w) was added and the mixture was stirred for 5 minutes. Hot water at 80° C. (45.07%) was added at a rate of 6/minute. When 0.15% of the total water charge remained to be added, xanthan gum (0.08%) was sprinkled onto the solution and the remaining water was added. The mixture was allowed to cool to 40° C., biocide (Acticide (MBL) 0.20%) was added with stirring and the mixture was packaged for use or distribution as required.

The resultant antioxidant was a solid in water suspension having a viscosity of 200-500 cP and pH 9.5-11.0, particle sized 95%<2 μm and a total solids content of 53-55%.

The invention claimed is:

1. A stabiliser for an organic polymer mixture, comprising a compound (a), a compound (b) and a compound (c) wherein;
   (a) is Antioxidant L;
   (b) is Antioxidant 1076; and
   (c) is Antioxidant 1520
      wherein the ratio by weight of (a):(b):(c) is in the range 5 to 30:5 to 30:5 to 30.

2. A stabilizer as claimed in claim 1, wherein the ratio by weight of (a):(b):(c) is 10:10:10.

3. A stabiliser as claimed in claim 1, wherein the ratio by weight of (a):(b):(c) is 20:10:20.

4. A stabiliser as claimed in claim 1, further comprising an aqueous solution or aqueous dispersion.

5. A stabiliser for an organic polymer mixture, comprising a compound (a) and a compound (c) wherein (a) and (c) are as follows:
   (a) is Antioxidant L; and
   (c) is Antioxidant 1520.

6. A stabiliser as claimed in claim 5, wherein the ratio by weight of (a):(c) is in the range of 4:1 to 1:1.

7. A stabiliser as claimed in claim 6, wherein the range is 3:1 to 1:1.

8. A stabiliser as claimed in claim 7, wherein the range is 2:1 to 1:1.

9. A stabiliser as claimed in claim 8, wherein the range is 1:1.

10. A stabiliser for an organic polymer mixture, comprising (b) Antioxidant 1076 (c) Antioxidant 1520.

11. A stabiliser as claimed in claim 10, wherein the ratio by weight of (b):(c) is in the range 4:1 to 1:1.

12. A stabiliser as claimed in claim 11, wherein the range is 3:1 to 1:1.

13. A stabiliser as claimed in claim 12, wherein the range is 2:1 to 1:1.

14. A stabiliser as claimed in claim 13, wherein the range is 1:1.

15. A stabiliser as claimed in claim 1, further comprising a phosphite antioxidant.

16. A stabiliser as claimed in claim 15, wherein the phosphite is selected from the group consisting of:
   tris (nonylphenyl) phosphite;
   tris (2,4-di-t-butyl phenyl) phosphite;
   other alkylaryl phosphites and mixtures thereof.

17. A method of preparation of a stabiliser as claimed in claim 1, comprising the steps of:
   heating a mixture of the compounds (a), (b), (c) to a temperature above 60° C. to form a molten mixture;
   adding a surfactant to the molten mixture;
   adding hot water to the molten mixture;
   stirring the resulting aqueous mixture; and
   optionally adding one or more further ingredients.

18. A method as claimed in claim 17, wherein the ratio by weight of (a):(b):(c) is 10:10:10.

19. A method as claimed in claim 17, wherein the ratio by weight of (a):(b):(c) is 20:10:20.

20. A method as claimed in claim 17, further comprising an aqueous solution or aqueous dispersion.

* * * * *